United States Patent [19]
Yokoyama et al.

[11] Patent Number: 6,087,528
[45] Date of Patent: Jul. 11, 2000

[54] PROCESS FOR PRODUCING HYDROXYALKYL MONOACRYLATE USING STANNOXANE CATALYSTS

[75] Inventors: Toshiharu Yokoyama; Yuuji Kawaragi, both of Yokohama; Kouya Murai, Yokkaichi, all of Japan

[73] Assignee: Mitsubishi Chemical Corporation, Tokyo, Japan

[21] Appl. No.: 09/083,964

[22] Filed: May 26, 1998

[30] Foreign Application Priority Data

May 30, 1997 [JP] Japan .................................. 9-157943

[51] Int. Cl.[7] .................................................. C07C 67/02
[52] U.S. Cl. ........................... 560/217; 560/204; 560/224
[58] Field of Search .................................. 560/204, 217, 560/224

[56] References Cited

U.S. PATENT DOCUMENTS

| | | |
|---|---|---|
| 3,642,877 | 2/1972 | Jayawant . |
| 4,281,175 | 7/1981 | Kametani . |
| 5,034,551 | 7/1991 | Vernon et al. . |
| 5,545,600 | 8/1996 | Knudsen et al. . |
| 5,554,785 | 9/1996 | Trapasso et al. . |
| 5,606,103 | 2/1997 | Trapasso et al. . |
| 5,610,313 | 3/1997 | Riondel et al. . |

FOREIGN PATENT DOCUMENTS

| | | |
|---|---|---|
| 0 455 390 A2 | 11/1991 | European Pat. Off. . |
| 1 518 572 | 7/1965 | Germany . |
| 5-76350 | 10/1985 | Japan . |

OTHER PUBLICATIONS

Database WPI; Section Ch, Week 8721; Derwent Pub. Ltd., Class A60, AN 87–148285.

*Primary Examiner*—Gary Geist
*Assistant Examiner*—Robert W. Deemie
*Attorney, Agent, or Firm*—Nixon & Vanderhye

[57] ABSTRACT

A process for producing hydroxyalkyl monoacrylate of the present invention, comprises the steps of: reacting acrylic acid or an acrylic acid derivative with alkane diol for esterification and/or transesterification therebetween in the presence of a reaction catalyst comprising a stannoxane compound; recovering said reaction catalyst from a liquid reaction product by extraction; and recycling the recovered reaction catalyst to a reaction system for said esterification and/or transesterification. The process of the present invention is an industrially useful process for producing hydroxyalkyl monoacrylate, which is excellent in reactivity, selectivity for an aimed product, stability of a reaction catalyst used and stability of a reaction substrate and product, and is improved so as to effectively recover and reuse the reaction catalyst.

18 Claims, No Drawings

PROCESS FOR PRODUCING HYDROXYALKYL MONOACRYLATE USING STANNOXANE CATALYSTS

BACKGROUND OF THE INVENTION

The present invention relates to a process for producing a hydroxyalkyl monoacrylate, and more particularly to an improved and industrially advantageous process for the production of a hydroxyalkyl monoacrylate, which is capable of effectively recovering a reaction catalyst for reuse thereof.

Hydroxyalkyl monoacrylates are compounds represented by the general formula of $CH_2=CHCOO(CH_2)_nOH$, wherein n is an integer of 1 to 10, and are useful as raw materials for polymers or copolymers having practically interested properties such as appropriate flexibility and hydrophilicity, because these compounds contain both hydrophobic alkyl units and hydrophilic hydroxyl groups in their molecules. In addition, it has been expected that the hydroxyalkyl monoacrylates are used in the form of crosslinkable polymers or copolymers in paint applications since hydroxyl groups thereof have a high reactivity.

It is known in the art that the hydroxyalkyl monoacrylates are produced by reacting acrylic acid or its derivative with alkane diol. For example, in German Patent No. 15118572, there is described a method of replacing a terminal group of alkane diol with an acrylic group by using a strong protonic acid such as sulfuric acid or hydrochloric acid as a reaction catalyst.

In addition, titanium alkoxides have been extensively used as catalysts for esterification or transesterification, and have also exhibited a high activity in the afore-mentioned reaction between acrylic acid or its derivative and alkane diol, and a high selectivity for the aimed product. In Japanese Patent Application Laid-open (KOKAI) No. 52-153913 (1977), there have been proposed a method of using a stannoxane compound as a reaction catalyst upon producing dimethylaminoethyl methacrylate by transesterification reaction. In Japanese Patent Publication (KOKOKU) No. 5-76350(1993), there have been proposed a method of using a halogen-substituted distannoxane-based catalyst as a high activity esterification catalyst. Further, in Japanese Patent Publication (KOKOKU) No. 46-39848(1971), there have been proposed a method of using dibutyl-n-tin oxide as a transesterification catalyst, and in Japanese Patent Application Laid-open (KOKAI) No. 7-97387(1995), there have been proposed a method of recovering a distannoxane catalyst from a mixed solution containing the distannoxane catalyst and saccharose-6-ester by extraction.

However, in the method described in German Patent No. 15118572, there arise problems such as corrosion of a reactor used due to existence of the strong acid catalyst, and decrease in selectivity for aimed hydroxyalkyl monoacrylate due to cyclization of the raw alkane diol and formation of high-boiling reaction products. In addition, the above-mentioned method inevitably requires complicated water-washing and neutralizing steps for separating the reaction catalyst from the reaction product.

In the method using the titanium alkoxide catalyst, although the titanium alkoxide catalyst shows a high catalytic activity and a high selectivity for the aimed product, there also arises such a problem that since the catalyst is highly hydrolyzable, the catalytic activity thereof is abruptly lost even in the presence of a very small amount of water. Therefore, when such a titanium alkoxide catalyst is used, it is required to completely remove water from the reaction system. Further, in the case of using the dibutyl-n-tin oxide catalyst, since the catalyst has a low solubility in a reaction substrate, it takes a long period of time until the catalytic activity thereof is sufficiently exhibited.

In the methods described in Japanese Patent Application Laid-open (KOKAI) No. 52-153913(1977) and Japanese Patent Publication (KOKOKU) No. 5-76350(1993), although there has been used the stannoxane catalyst which is excellent in catalytic activity, etc., in these publications, there are neither descriptions nor teaching concerning recovery and reuse of the catalyst, which are important when it is intended to industrially put these methods into practice.

More specifically, in Japanese Patent Application Laid-open (KOKAI) No. 52-153913(1977), although it is merely described that the reaction solution is distilled under reduced pressure to distill off the methacrylate as a reaction product, there are neither descriptions nor teachings concerning recovery and reuse of the stannoxane catalyst. In addition, in Japanese Patent Publication (KOKOKU) No. 5-76350 (1993), it is only described that the esterification catalyst is recovered from the distillation residue or the like and can be reused as it is.

Also, in Japanese Patent Application Laid-open (KOKAI) No. 7-97387(1995), there is only described a method of separating the catalyst upon the production of relatively stable esters such as saccharose-6-ester.

Meanwhile, according to the present inventors' knowledge as to the production of hydroxyalkyl monoacrylate using the stannoxane catalyst, it would be difficult to actually conduct the distillation and separation processes under a high temperature condition for recovering the catalyst. More specifically, in the case where the acrylic acid derivative or methacrylic acid derivative exists in the reaction system as a starting material or a reaction product, there arises a problem that the derivative not a little undergoes thermal polymerization or chemical deterioration when heated in the presence of the stannoxane catalyst. It is considered that such a problem is caused due to the fact that the hydroxyalkyl monoacrylate shows an extremely low thermal stability and an extremely high reactivity in the presence of the stannoxane catalyst.

Especially, in the case where alkyl diacrylate having a high unsaturated bond content always exists as an unreacted raw material or a by-product in the reaction solution together with an acid catalyst such as stannoxane-based catalyst in the production of the hydroxyalkyl monoacrylate by subjecting acrylic acid or alkyl diacrylate and alkane diol to esterification and/or transesterification, the above-mentioned problem becomes more remarkable.

As a result of the present inventors' earnest studies, it has been found that in the production of the hydroxyalkyl monoacrylate comprising subjecting acrylic acid or an acrylic acid derivative and alkane diol to esterification and/or transesterification, by using a specific stannoxane catalyst and recovering the catalyst by extraction, the above-mentioned problems can be readily overcome. The present invention has been attained on the basis of the finding.

SUMMARY OF THE INVENTION

It is an object of the present invention to provide an industrially useful process for producing hydroxyalkyl monoacrylate, which process is excellent in reactivity, selectivity for an aimed product, stability of a reaction catalyst used and stability of a reaction substrate and product, and is improved so as to effectively recover and reuse the reaction catalyst.

To accomplish the aim, in an aspect of the present invention, there is provided a process for producing hydroxyalkyl monoacrylate, which comprises:

reacting acrylic acid or an acrylic acid derivative represented by the general formula (I) or the general formula (II):

$$CH_2=CHCOOR \qquad (I)$$

(wherein R is an alkyl group)

$$CH_2=CHCOO(CH_2)_nOOCH=CH_2 \qquad (II)$$

(wherein n is an integer of 1 to 10)
with alkane diol represented by the general formula (III):

$$HO(CH_2)_nOH \qquad (III)$$

(wherein n is an integer of 1 to 10)
for esterification and/or transesterification therebetween in the presence of a reaction catalyst comprising a stannoxane compound represented by the general formula (IV):

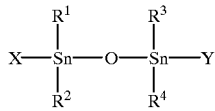

(IV)

wherein $R^1$, $R^2$, $R^3$ and $R^4$ are the same or different and are independently an alkyl group or a phenyl group which may be substituted; and X and Y are the same or different and are independently —OH, —O(CH$_2$)$_n$OH, —O(CH$_2$)$_n$OCOCH=CH$_2$, —OR, —OCOR, —OCOCH=CH$_2$ (wherein R is an alkyl group and n is an integer of 1 to 10), or a halogen atom;

recovering the reaction catalyst from a liquid reaction product by extraction; and recycling the recovered catalyst to a reaction system for the esterification and/or transesterification.

DETAILED DESCRIPTION OF THE INVENTION

The present invention will be described in detail below.

One of raw materials used in the esterification and/or transesterification according to the present invention, is acrylic acid or an acrylic acid derivative represented by general formula (I) or the general formula (II):

$$CH_2=CHCOOR \qquad (I)$$

(wherein R is an alkyl group)

$$CH_2=CHCOO(CH_2)_nOCOCH=CH_2 \qquad (II)$$

(wherein n is an integer of 1 to 10).

In the general formula (I), the alkyl group R may be selected from alkyl groups having usually 1 to 12 carbon atoms, preferably 1 to 8 carbon atoms. Specific examples of the acrylic acid derivatives represented by the general formula (I) may include methyl acrylate, ethyl acrylate, 2-ethylhexyl acrylate or the like.

In the general formula (II), n is an integer of 1 to 10, preferably 2 to 6. Specific examples of the acrylic acid derivatives represented by the general formula (II), i.e., alkyl diacrylates, may include ethyleneglycol diacrylate, butane-diol diacrylate, hexane-diol diacrylate, decane-diol diacrylate or the like. These alkyl diacrylate compounds are not only used as a raw material but also produced as a by-product, for example, when hydroxyalkyl monoacrylate is produced by the reaction between acrylic acid and the below-mentioned alkane diol. Therefore, the alkyl diacrylate compound always exits in a reaction system for the esterification and/or transesterification according to the present invention.

Another raw material used in the present invention is alkane diol represented by the general formula (III):

$$HO(CH_2)_nOH \qquad (III)$$

In the general formula (III), n is an integer of 1 to 10, preferably 2 to 6. Specific examples of the alkane diols represented by the general formula (III) may include ethylene glycol, butane diol, hexane diol, decane diol or the like.

The reaction catalyst used in the present invention is a stannoxane compound represented by the general formula (IV):

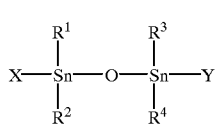

(IV)

In the general formula (IV), in the case where $R^1$, $R^2$, $R^3$ and $R^4$ are alkyl groups, the alkyl groups usually have 1 to 20 carbon atoms. Specific examples of the alkyl groups may include a methyl group, an ethyl group, a propyl group, a butyl group, a pentyl group, an octyl group, a dodecyl group, a stearyl group or the like. Alternatively, in the case where $R^1$, $R^2$, $R^3$ and $R^4$ are substituted or unsubstituted phenyl groups, substituents of the phenyl groups are usually alkyl groups. Specific examples of the alkyl groups as substituents of the phenyl groups may include those mentioned above with respect to $R^1$, $R^2$, $R^3$ and $R^4$. The alkyl groups or the substituted or unsubstituted phenyl groups may be the same or different. Especially, from the standpoints of recovery efficiencies for the catalyst upon extraction and separation processes after the reaction, and solubility of the catalyst, it is preferred to use alkyl groups having 4 to 12 carbon atoms and a phenyl group.

In the general formula (IV), X and Y are those selected from the group consisting of —OH, —O(CH$_2$)$_n$OH, —O(CH$_2$)$_n$OCOCH=CH$_2$, —OR, —OCOR, —OCOCH=CH$_2$, (wherein R is an alkyl group and n is an integer of 1 to 10), and a halogen atom. The integer n is preferably 2 to 6, and R is preferably an alkyl group having 1 to 8 carbon atoms. In addition, as the halogen atom, there may be exemplified Cl, Br or the like.

The stannoxane compounds can be readily produced, for example, by methods described in "Advance in Organometallic Chemistry", Vol. 5, p. 159(1967), or the like.

The ratio between the amount used of acrylic acid or acrylic acid derivatives represented by the general formulae (I) and (II) (both hereinafter referred to merely as "acrylic acid derivative"), and the amount used of alkane diol represented by the general formula (III) is not particularly restricted. In general, the acrylic acid derivative is used in more excessive amount relative to that of alkane diol, the higher the conversion of the alkane diol becomes. However, in such a case, the amount of hydroxyalkyl monoacrylate produced is decreased while the amount of alkyl diacrylate produced is increased. Accordingly, the ratio between the amounts of the two raw materials used may be appropriately selected in view of cost required for the extraction and separation steps after the reaction, acceptable purity of hydroxyalkyl monoacrylate as the aimed product, and the like.

In the present invention, the acrylic acid derivative may be used in an amount of usually 0.5 to 5 moles, preferably 0.5 to 2 moles (calculated as an acrylic group) based on one mole of the alkane diol. In the case where the amount of the acrylic acid derivative relative to that of the alkane diol is in such a range, the conversion of alkane diol is appropriately controlled, so that it becomes possible to maximize the amount of hydroalkyl monoacrylate in the reaction product, thereby enhancing productivity and a whole extraction efficiency.

Further, in the case where by appropriately controlling the conversion of alkane diol, the amount of hydroxyalkyl monoacrylate and alkyl diacrylate in the reaction product is maximized, the acrylic acid derivative is used in an amount of usually 2 to 50 moles, preferably 5 to 30 moles (calculated as an acrylic group) based on one mole of the alkane diol.

Also, in the case where the reaction product containing substantially another two components, i.e., hydroxyalkyl monoacrylate and alkane diol only, can be produced by converting the acrylic acid derivative at a high efficiency, the alkane diol is used in an amount of usually 2 to 20 moles, preferably 2 to 10 moles based on one mole of the acrylic acid derivative.

The amount of the stannoxane compound used as a reaction catalyst is usually 0.01 to 50 mole %, preferably 0.1 to 20 mole % based on the mole of acrylic acid as a raw material, alkyl acrylate, hydroxyalkyl acrylate or a mixture thereof.

In the present invention, a reaction solvent may be used, if necessary, though the use thereof is not particularly required. Examples of the reaction solvents usable may include aromatic hydrocarbons such as toluene or xylene; aliphatic hydrocarbons such as hexane, heptane, octane or decane; halogenated hydrocarbons such as tetracholoroethylene or chlorobenzene; oxygen-containing organic compounds such as tetrahydrofuran, dioxane or diethyleneglycol dimethyl ether; or the like.

Upon the reaction, in order to inhibit polymerization of the acrylic acid derivative as a raw material and hydroxyalkyl monoacrylate as the aimed product, it is preferred to add a polymerization inhibitor to the reaction system. As the polymerization inhibitors, there may be exemplified phenothiazine, hydroquinones, copper compounds such as copper salts of dialkyl-dithiocarbamate, or the like. In addition, by making molecular oxygen exist in the reaction system, the polymerization-inhibiting effect of the raw material and the product may be enhanced. Such a molecular oxygen may be continuously introduced into the reaction system by usually feeding air thereinto directly or after diluted with nitrogen or inert gas.

In accordance with the present invention, the esterification and/or transesterification can proceed at a high reactivity even under moderate conditions. Specifically, the reaction temperature used in the present invention is usually 60 to 150° C., preferably 70 to 130° C. When the reaction temperature is less than 60° C., a sufficient reactivity may not be obtained. On the other hand, when the reaction temperature is more than 150° C., undesirable side reactions such as polymerization may tend to be caused. The reaction time is usually 2 to 15 hours. At such a reaction time, the reaction can reach equilibrium. After reaching the equilibrium, unreacted raw materials such as acrylic acid or acrylic acid derivative and a reaction solvent are distilled off under reduced pressure. The thus obtained product can be transferred into subsequent extraction and separation steps.

Meanwhile, in the equilibrium reaction, the conversion of raw materials into the aimed product is adversely influenced by the existence of water or lower alcohols as by-products. Accordingly, when there is adopted a distillative reaction method in which the reaction is conducted while distilling off water or lower alcohols as by-products from the reaction system, the conversion of raw materials to the aimed product can be more suitably enhanced.

The water or lower alcohols as by-products can be removed by distillation under ordinary pressure or reduced pressure. Alternatively, these by-products can be removed by adding the other inert solvent (azeotropic solvent) to the reaction solution and subjecting the reaction solution to azeotropy. The removal of these by-products by addition of the azeotropic solvent is more advantageous because of less differences in boiling point between acrylic acid and water, and between lower acrylates and lower alcohols. In the case where the azeotropic solvent is the same as an extraction solvent, after separation of the azeotropic solvent, if necessary, from the mixed solution removed of water or alcohol and azeotropic solvent, the resultant reaction solution as it is may be transferred into the subsequent extraction step. In view of thermal stability of the product, it is preferred that the distillation temperature is not more than 130° C.

After removal of the low boiling components including acrylic acid, alkyl acrylic acid and the reaction solvent from the reaction solution by the distillation, the resultant reaction solution is subjected to extraction and separation steps, thereby separating alkyl diacrylate from a mixture of hydroxyalkyl monoacrylate and unreacted alkane diol. At this time, by using an appropriate extraction solvent, the catalyst component is selectively extracted together with the alkyl diacrylate from the reaction solution into the organic solvent phase.

Examples of the extraction solvents may include aliphatic hydrocarbons such as n-hexane, n-heptane, n-decane, i-octane or i-decane; alicyclic hydrocarbons such as cyclohexane; or aromatic hydrocarbons such as benzene, toluene, xylene or ethyl benzene. In addition, when two-component extraction solvent containing an organic solvent and water is used, the extraction efficiency can be further enhanced. Especially, liquid-liquid extraction using a n-heptane or n-hexane phase and a water phase, is more preferred because a high distribution coefficient and a high specific selectivity can be obtained.

Upon the extraction and separation steps, the alkyl diacrylate and the catalyst component are distributed into the organic phase, thereby separating these components from hydroxyalkyl monoacrylate as the aimed product. In the present invention, the organic phase containing the alkyl diacrylate and the catalyst component can be reused in the following manner:

(1) The organic phase is circulated to the esterification and/or transesterification reaction system as it is without any post-treatment thereof; or (2) After the organic phase is subjected to low-temperature distillation under reduced pressure to remove the organic solvent therefrom, the resultant distillation residue is circulated to the esterification and/or transesterification reaction system as it is.

As a result of the above-mentioned reuse of the organic phase, there can be obtained such an advantage that the process is considerably simplified.

As described above, the catalyst component is selectively transferred together with the alkyl diacrylate into the organic solvent phase by subjecting the liquid reaction product to extraction treatment using, for example, water/organic solvents. This is because the stannoxane compound as the catalyst component has a high resistance to hydrolysis and a high lipophilic property. Therefore, in accordance with the present invention, by using the stannoxane compound as a reaction catalyst, it is possible to produce hydroxyalkyl monoacrylate by much simpler method as compared to conventional methods, and to reuse the catalyst component substantially without loss.

The thus extracted and recovered catalyst can be reused without deterioration in its catalytic activity. However, it has been confirmed by Sn119-NMR analysis that the structure of the catalyst is gradually changed during long-term use. It has also been found that when a free carboxylic acid exists upon extraction and separation of the catalyst, the stability of the catalyst is enhanced, so that the change in structure of the catalyst can be inhibited and the extraction efficiency of transferring the catalyst into the organic phase can be further enhanced, thereby increasing a stability of the catalyst. As a free carboxylic acid, there may be exemplified aliphatic carboxylic acid such as monocarboxylic acid, dicarboxylic acid or tricarboxylic acid. Among them, the monocarboxylic acid is preferably used. As a monocarboxylic acid, there may be exemplified acrylic acid, acetic acid or the like. In addition, it is preferably acrylic acid.

Especially, in the case where an acyloxy distannoxane derivative is used as the catalyst, it is preferred that carboxylic acids as a ligand of the derivative be used as the free carboxylic acid. In a method of the extraction in the presence of the free carboxylic acid, there may be exemplified (i) a method of adding a carboxylic acid upon the extraction, or (ii) a method of making a free carboxylic acid exist at the extraction by using acrylic acid as a raw material.

When the free carboxylic acid is made to exist in the reaction system specifically upon the extraction, it is preferred that an acyloxy group-containing compound is added in an amount of usually 1 to 10 moles, preferably 2 to 6 moles (calculated as an acyloxy group) based on one mole of Sn atom to the reaction solution. When an excess amount of the acyloxy group-containing compound is added, acid may be accumulated in the reaction system, thereby subsequently requiring complicated separation procedure thereof.

The acyloxy group-containing compounds described above may include both free carboxylic acid itself and an Sn compound to which an acyloxy group is coordinated. As the acyloxy groups, there may be exemplified an acrylic group, an acetoxy group or the like. The amount of the acyloxy group existing upon the extraction can be calculated as a total amount of acyloxy group in the carboxylic acid added and that coordinated to the Sn compound, the latter being obtained by Sn119-NMR measurement. The amount of the acyloxy group existing upon the extraction can also be determined by titrating the water phase obtained after the extraction, with alkali by ordinary methods.

Further, in the case where two-component solvent containing an organic solvent and water is used as an extraction solvent, it is preferred that the amount of the carboxylic acid be controlled such that the pH of the water phase separated after the extraction is 2 to 4. It is considered that the free carboxylic acid existing upon the extraction has a equilibrium relationship with the acyloxy group coordinated to Sn atom. Thus, due to the existence of the free carboxylic acid, the Sn catalyst can be maintained in a stable condition and readily extracted into an organic solvent.

As an extraction apparatus, a continuous extraction apparatus such as a mixer seter-type extraction apparatus, a rotating disc-type extraction apparatus, pulsation-type extraction apparatus, a packed column-type extraction apparatus may be exemplified. The number of the theoretical plates in the extraction apparatus is usually 1 to 100 plates, preferably 3 to 50 plates.

After the extraction, an excessive amount of carboxylic acid remaining in the water phase containing hydroxyalkyl monoacrylate as a reaction product can be readily removed by ordinary methods such as alkali treatment. Further, the hydroxyalkyl monoacrylate-containing phase as a liquid residue remaining after separation of the catalyst may be subjected to purifying treatments such as distillation or extraction, if required, to recover high purity hydroxyalkyl monoacrylate.

In the process for the production of hydroxyalkyl monoacrylate according to the present invention, by using the stannoxane compound as a reaction catalyst, it is possible to obtain the aimed product with a high catalytic activity and a high selectivity. Further, by subjecting the reaction solution to extraction procedure, the reaction catalyst can be recovered together with alkane-diol diacrylate with a high extraction efficiency for reuse thereof. Therefore, the process of the present invention can considerably simplify the production process, thereby achieving a high profitability.

EXAMPLES

The present invention will be described in more detail by examples, but these examples are not intended to limit the scope of the present invention.

Reference Example 1

14.94 g (60 mmol) of dibutyl tin oxide and 6.08 g (20 mmol) of dibutyl tin dichloride were reacted with each other in a mixed solvent of 190 ml of ethanol and 10 ml of water at 80° C. for 6 hours under reflux. After completion of the reaction, ethanol and water were distilled off to obtain a catalyst residue. The catalyst residue was dissolved in 75 ml of n-hexane to prepare a homogeneous solution. The resultant solution was cooled to obtain a crystallized white solid. The obtained white solid was filtered out by passing the solution through a 0.8 $\mu$m-Millipore filter, and then washed with cooled hexane several times. Thereafter, the obtained solid was dried at 60° C. for 6 hours under reduced pressure to obtain distannoxane compound (BCH) shown below in Table 1. Incidentally, the measuring conditions for identification data (NMR spectrum) in Table 1 are shown below.

Measuring conditions of Sn-NMR
 Type of device used: Varian UNITY-300
 Observ.: 119 Sn;
 Solv.: Benzen-d6;
 Reference Sn: $Sn(CH_3)_4$;
 Frequency: 111.862 MHz;
 Acquisition time: 0.64 sec.;
 Relaxation time: 0.20 sec.

Reference Example 2

The same procedure as defined in Reference Example 1 was conducted except that 21.67 g (60 mmol) of dioctyl tin oxide was used instead of dibutyl tin oxide, thereby producing a distannoxane compound. Further, the thus produced distannoxane compound was treated with ethanol to obtain a distannoxane compound (OCE) shown in Table 1.

Reference Example 3

36.12 g (100 mmol) of dioctyl tin oxide and 6.00 g (100 mmol) of acetic acid were reacted with each other in 100 ml of toluene for 2 hours under reflux and dewatering conditions. After completion of the reaction, toluene was distilled off to obtain a viscous residue. The viscous residue was dissolved in 65 ml of hexane to prepare a homogeneous solution. The solution was cooled with dry ice to obtain a crystallized white solid. The obtained white solid was filtered out by passing the solution through a 0.8 μm-Millipore filter, and then washed with cooled hexane several times. Thereafter, the solid was dried at 60° C. for 8 hours under reduced pressure to obtain a distannoxane compound (OAA) shown below in Table 1.

Reference Example 4

18.06 g (50 mmol) of dioctyl tin oxide, 3.61 g (50 mmol) of acrylic acid and 7 mg of phenothiazine were reacted with each other in 75 ml of toluene for 4 hours under reflux and dewatering conditions. After completion of the reaction, toluene was distilled off to obtain a light yellow-colored viscous liquid residue. The viscous liquid residue was dissolved in 60 ml of n-hexane to prepare a homogeneous solution. The solution was cooled with dry ice to obtain a crystallized white solid. The obtained white solid was separated from the solution by using an injector and then washed with cooled hexane several times. Thereafter, the solid was dried at 60° C. for 8 hours under reduced pressure to obtain a distannoxane compound (OLL) shown below in Table 1.

Reference Example 5

20.09 g (75 mmol) of dioctyl tin oxide, 6.653 g (37.5 mmol) of dimethyl carbonate and 0.5 ml of ethanol were reacted with each other in 100 ml of toluene for 4 hours under reflux. After completion of the reaction, toluene was distilled off to obtain a white viscous residue. The viscous residue was dissolved in 60 ml of hexane to prepare a homogeneous solution. The solution was cooled with dry ice to deposit a crystallized white solid. The obtained white solid was filtered out by passing the solution through a 0.8 μm-Millipore filter while cooling, and then washed with cooled hexane several times. Thereafter, the solid was dried at 60° C. for 8 hours under reduced pressure to obtain a distannoxane compound (OMM) shown below in Table 1.

Reference Example 6

5.37 g (6.5 mmol) of the distannoxane compound (OAA) obtained in Reference Example 3 and 5.00 g (6.5 mmol) of the distannoxane compound (OMM) obtained in Reference Example 5 were reacted with each other in 60 ml of hexane for 2 hours under reflux. After completion of the reaction, hexane was distilled off to obtain a white viscous residue. The viscous residue was dissolved in 60 ml of hexane to prepare a homogeneous solution. The solution was cooled with dry ice to deposit a crystallized white solid. The obtained white solid was filtered out by passing the solution through a 0.8 μm-Millipore filter, and then washed with cooled hexane several times. Thereafter, the solid was dried at 60° C. for 8 hours under reduced pressure to obtain a distannoxane compound (OAM) shown below in Table 1.

TABLE 1

| Reference Example No. | Distannoxane compound | Identification data (NMR spectrum) | Code |
|---|---|---|---|
| Reference Example 1 | Cl—Sn(R)(R)—O—Sn(R)(R)—OH, R = butyl | 119Sn-NMR; δ = −162.9 ppm, −179.5 ppm | BCH |
| Reference Example 2 | Cl—Sn(R)(R)—O—Sn(R)(R)—OCH$_2$CH$_3$, R = octyl | 119Sn-NMR; δ = −154.1 ppm, −178.6 ppm | OCE |
| Reference Example 3 | AcO—Sn(R)(R)—O—Sn(R)(R)—OAc, R = octyl, Ac = CH$_3$CO | 119Sn-NMR; δ = −218.9 ppm, −229.9 ppm | OAA |
| Reference Example 4 | CH$_2$=CHCOO—Sn(R)(R)—O—Sn(R)(R)—OCOCH=CH$_2$, R = octyl | 119Sn-NMR; δ = −216.0 ppm, −225.8 ppm | OLL |
| Reference Example 5 | CH$_3$O—Sn(R)(R)—O—Sn(R)(R)—OCH$_3$, R = octyl | 119Sn-NMR; δ = −174.6 ppm, −186.7 ppm | OMM |

TABLE 1-continued

| Reference Example No. | Distannoxane compound | Identification data (NMR spectrum) | Code |
|---|---|---|---|
| Reference Example 6 | AcO—Sn(R)(R)—O—Sn(R)(R)—OCH$_3$<br>R = octyl<br>Ac = CH$_3$CO | 119Sn-NMR;<br>δ = -181.9 ppm,<br>-216.8 ppm | OAM |

Example 1

2.34 g (4.38 mmol) of the distannoxane compound (BCH) obtained in Reference Example 1, 238.8 g (2.774 mol) of methyl acrylate, 135.3 g (1.501 mol) of 1,4-butane diol (hereinafter referred to merely as "1,4BG") and 0.6 g of phenothiazine were charged into a separable flask equipped with an agitator and a reaction distilling tube, and reacted with each other at a temperature of 86 to 120° C. for 6 hours while distilling off methanol produced.

The obtained reaction solution was analyzed by gas chromatography (GC). As a result of the analysis, it was determined that the conversion of 1,4BG was 83.2 mol %; the conversion of methyl acrylate was 65.9 mol %; the selectivity of 4-hydroxybutyl acrylate (hereinafter referred to merely as "4HBA") based on 1,4BG was 59.0 mol %; the selectivity of 1,4-butane diol diacrylate (hereinafter referred to merely as "BDA") was 41.0 mol %; and no other by-products were detected. Incidentally, the gas chromatography analysis was conducted under the conditions shown below.

Conditions of Gas Chromatography Analysis

Column used: TC-WAX capillary column manufactured by gas chromatography Science Co., Ltd.;

30 mL×0.25 mm I.D.×0.25 μm;

Retained at 60° C. for 8 min. and then heated at a rate of 5° C./min.;

Inj. temperature: 250° C.;

Carrier gas: Argon;

Split ratio: 79; Detector used: FID

Next, the reaction solution was subjected to distillation treatment at 120° C. while reducing the pressure applied thereon from ordinary pressure to 3 mmHg, thereby distilling off unreacted methyl acrylate. Thereafter, 241.2 g of the concentrated reaction solution was mixed with 240 g of desalted water and 960 g of n-heptane, and the mixed solution was subjected to extraction treatment at room temperature, i.e., the solution was allowed to stand for a sufficient period of time to separate the solution into two phases. The obtained water phase was subjected again to extraction treatment by adding heptane thereto in an amount of 2 times by weight based on the amount of the water phase, and the extraction treatment was repeated four times in total. The resultant heptane phase was concentrated to finally obtain 108.0 g of a catalyst-containing BDA solution.

Next, by repeatedly using the obtained catalyst-containing BDA solution, the following reaction was conducted. That is, 108.0 g of the catalyst-containing BDA solution (containing 0.53 mol of BDA), 147.4 g (1.71 mol) of methyl acrylate and 87.4 g (0.91 mol of 1,4BG) were charged into a separable flask equipped with an agitator and a reaction distilling tube, and reacted with each other at a temperature of 86 to 120° C. for 5 hours while distilling off methanol produced, in the same manner as in the initial reaction.

The obtained reaction solution was analyzed by gas chromatography. As a result of the analysis, it was determined that the conversion of 1,4BG was 82.0 mol %; the conversion of methyl acrylate was 64.3 mol %; the selectivity of 4HBA based on 1,4BG was 57.8 mol %; and the selectivity of BDA was 42.2 mol %. Notwithstanding the reaction time was shortened, the results of the reaction were almost identical with those of the initial reaction. Incidentally, the amount of Sn transferred into the water phase in the extraction of the initially obtained reaction solution was measured by an inductively coupled plasma (ICP) analysis. As a result of the analysis, it was determined that the amount of Sn in the water phase was not more than 30 ppm. This indicated that not less than 99.5% of the stannoxane compound used in the initial reaction was extracted into the heptane phase and recycled to the reaction system.

Comparative Example 1

Methyl acrylate and 1,4BG were subjected to transesterification reaction in the same manner as described in Example 1. Thereafter, unreacted methyl acrylate was removed from the reaction solution to obtain a concentrated solution. 118.2 g of the thus obtained concentrated reaction solution containing 9.59 g of 1,4BG, 52.27 g of 4HBA and 58.88 g of BDA was distilled under a reduced pressure of 13 mmHg in an oil bath maintained at 135° C. to recover the catalyst and BDA.

When the overhead temperature of 117 to 120° C. was reached, distillates started to be generated. One hour after commencement of the distillation, the generation of distillates was stopped, whereupon a liquid still residue was changed to gelatinous polymers. The obtained distillates (62.46 g) were subjected to gas chromatography analysis. As a result of the analysis, it was determined that the distillates contained 8.79 g of 1,4BG, 29.13 g of 4HBA and 24.54 g of BDA. However, it was determined that 49.9% by weight of 4HBA and BDA used as raw materials in the reaction were changed to polymers. Further, it was extremely difficult to recover the catalyst component from the polymers.

Reference Example 7

10 g of a 4HBA reagent (produced by Aldrich Chemical Co., Inc.), and 1 mg of the distannoxane compound (BCH) obtained in Reference Example 1 were charged into a Schlenk tube, and heated at a constant temperature of 120° C. for 6 hours while stirring. The change of the tube content with time was traced by gas chromatography. Under the above-mentioned conditions, the concentration of 4HBA was linearly decreased finally up to 81%.

Example 2

15.0 g (18.2 mmol) of the distannoxane compound (OAA) obtained in Reference Example 3, 90 ml of methyl acrylate, 60 ml of 1,4BG and 0.2 g of phenothiazine were charged into a flask equipped with an agitator and a cooling tube, and reacted with each other at a temperature of 80 to 82° C. for 3 hours without distilling off methanol produced. The obtained reaction solution was analyzed by gas chromatography.

Next, the reaction solution was subjected to distillation treatment at a temperature of 90° C. while reducing the pressure applied thereto from ordinary pressure to 3 mmHg, thereby distilling off unreacted methyl acrylate. Thereafter, 97.3 g of the concentrated reaction solution was mixed with 100 g of desalted water and 400 g of n-heptane, and the mixed solution was subjected to extraction treatment at room temperature, i.e., the mixed solution was allowed to stand for a sufficient period of time to separate the solution into two phases. The obtained water phase was subjected again to extraction treatment by adding heptane thereto in an amount of 2 times by weight based on the amount of the water phase, and the extraction treatment was repeated four times in total. The resultant heptane phase was concentrated to finally obtain 33.3 g of a catalyst-containing BDA solution.

Next, by repeatedly using the obtained catalyst-containing BDA solution, the following reaction was conducted. That is, the catalyst-containing BDA solution was replenished with methyl acrylate and 1,4BG such that the amounts of respective raw materials were identical to those used in the initial reaction, taking into consideration that one mole of BDA corresponds to one mole of 1,4BG and 2 moles of methyl acrylate. The mixture was reacted under the same conditions as in the initial reaction. The obtained reaction solution was analyzed by gas chromatography.

Next, after distilling off unreacted methyl acrylate, the reaction solution was subjected to extraction treatment using water and heptane in the same manner as in the initial extraction procedure, thereby obtaining a concentrated catalyst-containing BDA solution. The above reaction and extraction were repeated seven times in total while replenishing only raw materials except for the stannoxane catalyst and phenothiazine as a polymerization inhibitor to the reaction solution. The molar ratios between 1,4BG, 4HBA and BDA in reaction solutions obtained in these repeated reactions are shown in Table 2.

TABLE 2

| Repeated reactions | 1, 4BG (mol %) | 4HBA (mol %) | BDA (mol %) |
|---|---|---|---|
| First reaction | 34.6 | 50.6 | 14.8 |
| Second reaction | 30.9 | 49.7 | 19.3 |
| Third reaction | 28.1 | 51.7 | 20.2 |
| Fourth reaction | 29.8 | 49.0 | 21.2 |
| Fifth reaction | 28.1 | 50.9 | 21.0 |
| Sixth reaction | 28.8 | 49.7 | 21.5 |
| Seventh reaction | 28.0 | 50.0 | 22.0 |

Example 3

10.0 g (12.6 mmol) of the distannoxane compound (OAM) obtained in Reference Example 6, 60 ml of methyl acrylate, 40 ml of 1,4BG and 135 mg of phenothiazine were charged into a flask equipped with an agitator and a cooling tube, and reacted with each other at a temperature of 80 to 82° C. for 3 hours without distilling off methanol produced. The obtained reaction solution was analyzed by gas chromatography.

Next, the reaction solution was subjected to distillation treatment at 90° C. while reducing the pressure applied thereto from ordinary pressure to 3 mmHg, thereby distilling off unreacted methyl acrylate. Thereafter, 68.19 g of the concentrated reaction solution was mixed with 70 g of desalted water and 280 g of n-heptane, and then the mixed solution was subjected to extraction treatment at room temperature, i.e., allowing the mixed solution to stand for a sufficient period of time to separate the solution into two phases. The obtained water phase was subjected again to extraction treatment by adding heptane thereto in an amount of 2 times by weight based on the amount of the water phase, and the extraction treatment was repeated four times in total. The resultant heptane phase was concentrated to finally obtain 24.71 g of a catalyst-containing BDA solution.

Next, by repeatedly using 22.24 g of the obtained catalyst-containing BDA solution, the following reaction was conducted. That is, the catalyst-containing BDA solution was replenished with 41 ml of methyl acrylate and 31 ml of 1,4BG such that the amounts of respective raw materials were identical to those used in the initial reaction, taking into consideration the amount of BDA in the catalyst-containing BDA solution. The mixture was reacted under the same conditions as used in the initial reaction. The obtained reaction solution was analyzed by gas chromatography. The molar ratios between 1,4BG, 4HBA and BDA in reaction solutions obtained in these repeated reactions are shown in Table 3.

TABLE 3

| Repeated reactions | 1, 4BG (mol %) | 4HBA (mol %) | BDA (mol %) |
|---|---|---|---|
| First reaction | 38.6 | 46.2 | 15.2 |
| Second reaction | 34.2 | 50.2 | 15.6 |

Reference Example 8

10.0 mmol of each of the distannoxane compounds obtained in Reference Examples 1 to 6, 60 ml (about 670 mmol) of methyl acrylate, 40 ml (about 445 mmol) of 1,4BG and 135 mg of phenothiazine were charged into a flask equipped with an agitator and a cooling tube, and reacted with each other for 3 hours in an oil bath maintained at 90° C. without distilling off methanol produced. The obtained reaction solution was analyzed by gas chromatography to determine amounts of 4HBA, BDA and unreacted 1,4BG contained in the reaction solution. The molar ratios between these three compounds are shown in Table 4.

TABLE 4

| Stannoxane compounds | Substituents | | | 1, 4BG (mol %) | 4HBA (mol %) | BDA (mol %) |
|---|---|---|---|---|---|---|
| | R | X | Y | | | |
| BCH (Reference Example 1) | C4 | Cl | OH | 34.6 | 50.6 | 14.8 |
| OCE (Reference Example 2) | C8 | Cl | $C_2H_5$ | 30.9 | 49.7 | 19.3 |
| OAA (Reference | C8 | OAc | OAc | 28.1 | 51.7 | 20.2 |

TABLE 4-continued

| Stannoxane compounds | Substituents R | X | Y | 1, 4BG (mol %) | 4HBA (mol %) | BDA (mol %) |
|---|---|---|---|---|---|---|
| Example 3) | | | | | | |
| OLL (Reference Example 4) | C8 | AA | AA | 29.8 | 49.0 | 21.2 |
| OAM (Reference Example 5) | C8 | OAc | OCH₃ | 28.1 | 50.9 | 21.0 |
| OMM (Reference Example 6) | C8 | OCH₃ | OCH₃ | 28.8 | 49.7 | 21.5 |

Example 4

180 g (2 mol) of 1,4-butane diol, 172 g (2 mol) of methyl acrylate (hereinafter referred to merely as "AEM"), 0.8 g of phenothiazine and 10.56 g (0.0128 mol; 0.0256 mol calculated as Sn atom) of tetraoctyldiacetoxy distannoxane (OAA) were charged into a 500 ml flask, heated in an oil bath while blowing air thereinto, and reacted with each other at 83° C. for 5 hours under reflux. After completion of the reaction under reflux, the obtained reaction solution was analyzed by gas chromatography to determine a composition thereof. The results of the analysis are as follows.

| 1, 4BG | 106 g (1.17 mol) |
|---|---|
| 4HBA | 93 g (0.64 mol) |
| BDA | 19 g (0.10 mol) |
| AEM | 95 g (1.1 mol) |

The percentage of the molar amount of 4HBA produced based on the molar amount of 1,4BG charged was 32%.

Comparative Example 2

The same procedure as defined in Example 4 was conducted except that the catalyst was replaced with 7.65 g (0.0128 mol; 0.0256 mol calculated as Sn atom) of bis(tributyl tin)oxide. After the reaction under reflux was conducted for 5 hours, the obtained reaction solution was analyzed by gas chromatography to determine a composition thereof. The results of the analysis are as follows.

| 1, 4BG | 164 g (1.82 mol) |
|---|---|
| 4HBA | 16 g (0.11 mol) |
| AEM | 162 g (1.88 mol) |

The percentage of the molar amount of 4HBA produced based on the molar amount of 1,4BG charged was 5.5%. It was determined that the reaction rate of Comparative Example 2 was extremely lower than that of Example 4.

Comparative Example 3

38.6 g (0.43 mol) of 1,4BG, 60.2 g (0.7 mol) of AEM, 0.14 g of phenothiazine and 9.1 g (0.025 mol) of dioctyl tin oxide as a catalyst were charged into a flask, and reacted with each other in an oil bath at a temperature of 80 to 82° C. for 3 hours under reflux while blowing a small amount of air thereinto.

The obtained reaction solution was distilled at 90° C. under reduced pressure to recover unreacted AEM and methanol, thereby obtaining 58.8 g of a liquid still residue. 60 ml of water was added to the liquid still residue, so that a solid was deposited. The deposited solid still remained even after adding 240 ml of heptane to the residue. This indicated that it was impossible to separate the liquid still residue by liquid-liquid extraction and separation method. 4.7 g of the solid deposited was isolated by filtering, and dissolved in acetic acid to measure Sn119-NMR spectrum thereof. As a result, it was considered that the solid was a decomposed product of the catalyst. According to the calculation based on the weight of the isolated solid, it was determined that about 50% of the catalyst initially used was deposited as a solid. As a result, it was determined that dioctyl tin oxide had a low stability to water and was unable to be separated from the reaction solution by extraction method.

Example 5

5,410 g (60 mol) of 1,4BG, 4,650 g (54 mol) of AEM, a hexane solution containing 35% by weight of the distannoxane catalyst (OLL) and 72 g of phenothiazine were charged into a 20-liter stainless steel reactor to which a distillation column filled with ¼" macmahon was attached. The content of the reactor was reacted and distilled at a temperature of 80 to 90° C. while continuously feeding hexane into the reactor and while distilling methanol produced out of the reaction system. After completion of the reaction, 8,810 g of the reaction solution as bottoms was obtained. The reaction solution was analyzed by gas chromatography to determine a composition thereof. The results of the analysis are as follows.

| 1, 4BG | 1,780 g (19.8 mol) |
|---|---|
| 4HBA | 4,017 g (27.9 mol) |
| BDA | 1,762 g (8.8 mol) |
| Hexane | 490 g |

100 g of the reaction solution was sampled, and mixed with x g of water and y ml of hexane, wherein x and y are shown below in Table 5, thereby subjecting the reaction solution to repeated extraction procedures. Thereafter, 4HBA was extracted from the obtained water phase using toluene or dichlorometahne as an extraction solvent. The solvent was removed by distillation from the resultant extract to obtain a crude 4HBA. The content of Sn in the crude 4HBA was determined by calculation. The data with respect to various values of x and y are shown in Table 5.

As is apparent from Table 5, although appropriate amounts of BDA and the catalyst were extracted without using water as an extraction solvent, a higher extraction efficiency was achieved when the extraction was conducted in the presence of water.

TABLE 5

| Weight ratio of water added relative to 4HBA | Number of extractions with hexane (x, y*) | Content of BDA in 4HBA (%) | Content of Sn in 4HBA (ppm) | Percentage of extraction into hexane phase (%) | |
|---|---|---|---|---|---|
| | | | | BDA | Sn |
| 0 | 500 ml × 4 | 1.3 | 80 | 97 | 99.2 |
| 2 | 400 ml × 4 | 0.3 | 8 | 99.3 | 99.92 |
| 8 | 200 ml × 3 | 0.3 | 2 | 99.3 | 99.98 |

Note *: Amount of hexane used based on 100 g of the reaction solution.

Example 6-1

1,350 g (15 mol) of 1,4BG, 1,419 g (16.5 mol) of AEM, 90 g of a distannoxane catalyst (OAA), 2 g of phenothiazine and 1,080 g of n-hexane were charged into a 5-liter flask, and reacted with each other in a distillation column filled with 3 mmφ-coil pack at a temperature of 70 to 100° C. under ordinary pressure while distilling off methanol produced. After the reaction was conducted for 15 hours, there was obtained 2,306 g of the reaction solution containing 550 g of 1,4BG, 990 g of 4HBA and 380 g of BDA.

200 g of the thus obtained reaction solution (containing 7.8 g of the distannoxane catalyst; 18.9 mmol calculated as Sn) was mixed with 200 g of water, and subjected to batch extraction process using 800 ml of n-heptane as an extraction solvent and a separatory funnel. After the n-heptane phase was separated, the pH of the remaining water phase was measured, and it was determined that the water phase had a pH of 4.1. Further, the extraction of the water phase with n-heptane was repeated four times to extract and transfer BDA and the catalyst into the heptane phase. The extraction interface between the respective phases was clear and the water phase was transparent.

The obtained heptane extracts were distilled together under reduced pressure to remove heptane as an extraction solvent therefrom, thereby obtaining a concentrated solution containing the catalyst and BDA. The obtained concentrated solution was analyzed by an atomic absorption spectroscopy. As a result of the analysis, it was determined that not less than 98% of Sn derived from the Sn catalyst initially charged was recovered.

340 g of the water phase after extracted with n-heptane was further subjected to extraction with 340 ml of toluene. The toluene extraction was repeated four times. The obtained toluene extracts were washed together with 120 ml of water in total. The toluene phase was distilled under reduced pressure by a rotary evaporator to remove toluene therefrom. Thereafter, the resultant liquid bottoms containing 4HBA were analyzed by an atomic absorption spectroscopy. As a result of the analysis, it was determined that the liquid bottoms contained 23 ppm of Sn. This indicated that 99.89% of Sn derived from the Sn catalyst initially charged was removed therefrom. The results are shown in Table 6.

Example 6-2

The same procedure as defined in Example 6-1 was conducted except that when the reaction solution was subjected to extraction with n-heptane, 1.3 g of acrylic acid (corresponding to one equivalent based on Sn) was added thereto. The results are shown in Table 6.

Example 6-3

The same procedure as defined in Example 6-1 was conducted except that when the reaction solution was subjected to extraction with n-heptane, 2.7 g of acrylic acid (corresponding to two equivalents based on Sn) was added thereto. The results are shown in Table 6.

Example 6-4

The same procedure as defined in Example 6-1 was conducted except that when the reaction solution was subjected to extraction with n-heptane, 6.8 g of acrylic acid (corresponding to five equivalents based 68.

TABLE 6

| | Example 6-1 | Example 6-2 | Example 6-3 | Example 6-4 |
|---|---|---|---|---|
| Amount of acyloxy group existing (moles/Sn) | 0.5 | 1.5 | 2.5 | 5.5 |
| Content of Sn in 4HBA after concentration (ppm) | 23 | 3.8 | 1.5 | 0.5 |
| Extraction efficiency of Sn (%) | 99.89 | 99.98 | 99.99 | 99.99 |
| Condition of extraction interface | Slightly white suspended matters | Light turbidity | Very light turbidity | Clear |
| pH of water phase | 4.1 | 3.3 | 3.2 | 2.9 |

As is apparent from Table 6, although a considerable amount of the catalyst was able to be extracted without addition of acid, it was determined that the addition of acid resulted in not only further enhancing an extraction efficiency of the catalyst, and also reducing a content of Sn in the 4HBA product.

Incidentally, in Table 6, the amount of acyloxy groups existing in the reaction system was calculated as a sum of the amount of acyloxy groups coordinated to Sn in the reaction solution before the addition of acid, and the amount of carboxylic acid added. The amount of acyloxy groups coordinated to Sn in the reaction solution before the addition of acid, was obtained as follows.

That is, the measurement showed that the amount of an acid value in the reaction solution was not more than 200 ppm (calculated as acetic acid), which corresponded to not more than 0.1 mole of a free acid based on one mole of Sn atom. In addition, the Sn 119-NMR analysis showed that the percentage of Sn atoms to which one acyloxy group was coordinated, was 50% of whole Sn atoms (calculated as total percentages of those ranging from −205 to −235 ppm), and no Sn atom to which two acyloxy groups were coordinated (corresponding to those ranging from −150 to −170 ppm) was observed. Accordingly, an average number of acyloxy groups coordinated to Sn atom was considered to be 0.5.

What is claimed is:

1. A process for producing hydroxyalkyl monoacrylate, comprising the steps of:

(a) reacting acrylic acid or an acrylic acid derivative represented by the general formula (I) or the general formula (II):

$$CH_2\!\!=\!\!CHCOOR \tag{I}$$

wherein R is an alkyl group, $$CH_2\!\!=\!\!CHCOO\,(CH_2)_n OCOCH\!\!=\!\!CH_2 \tag{II}$$

wherein n is an integer of 1 to 10,
   with alkane diol represented by the general formula (III):

$$HO(CH_2)_n OH \tag{III}$$

wherein n is an integer of 1 to 10,
   for esterification, transesterification or combination of esterification and transesterification therebetween in the presence of a reaction catalyst comprising a stannoxane compound represented by the general formula (IV):

(IV)

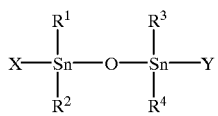

wherein $R^1$, $R^2$, $R^3$ and $R^4$ are the same or different and are independently an alkyl group or a phenyl group which may be substituted; and X and Y are the same or different and are independently a substituent selected from the group consisting of —OH, —O(CH$_2$)$_n$OH, —O(CH$_2$)$_n$OCOCH=CH$_2$, —OR, —OCOR or —OCOCH=CH$_2$, wherein R is an alkyl group and n is an integer of 1 to 10, and a halogen atom;

(b) separating said reaction product by extraction into a water phase containing hydroxyalkyl monoacrylate and an organic solvent phase containing said reaction catalyst; and (c) recycling the organic solvent phase containing said reaction catalyst to a reaction system for said esterification, transesterification or combination of esterification and transesterification.

2. A process according to claim 1, wherein said catalyst is recovered together with alkyl diacrylate.

3. A process according to claim 1, wherein said extraction is conducted in a two-component extraction solvent containing an organic solvent and water.

4. A process according to claim 3, wherein said organic solvent used in said two-component extraction solvent is at least one selected from the group consisting of aliphatic hydrocarbons and alicyclic hydrocarbons.

5. A process according to claim 4, wherein said organic solvent used in said two-component extraction solvent is n-heptane or n-hexane.

6. A process according to claim 3, wherein the amount of water is 1 to 10 parts by weight based on one part by weight of hydroxyalkyl monoacrylate to be extracted and separated.

7. A process according to claim 1, wherein the substituents $R^1$ to $R^4$ of said stannoxane compound represented by the general formula (IV) are selected from alkyl groups having 4 to 12 carbon atoms.

8. A process according to claim 1, wherein the substituents X and Y of said stannoxane compound represented by the general formula (IV) are —OCOR or —OCOCH=CH$_2$, wherein R is an alkyl group and n is an integer of 1 to 10.

9. A process according to claim 1, wherein the extraction is conducted in the presence of free carboxylic acid.

10. A process according to claim 9, wherein said carboxylic acid is acetic acid or acrylic acid.

11. A process according to claim 9, wherein the extraction is conducted in the presence of a compound containing an acyloxy group, and the amount of the acyloxy group is 1 to 10 moles based on one mole of Sn atom in the liquid reaction product.

12. A process according to claim 1, wherein the amount of the acrylic acid or acrylic acid derivative is 0.5 to 5 moles, calculated as an acrylic group, based on one mole of alkane diol.

13. A process according to claim 1, wherein said alkane diol is 1,4-butane diol.

14. A process according to claim 1, wherein said esterification, transesterification or combination of esterification and transesterification is conducted by distillation while distilling off water or alcohol as by-products.

15. A process according to claim 1, wherein after said catalyst is extracted and recovered from the liquid reaction product into said organic solvent, the remaining water phase is subjected to extraction using an azeotropic solvent to obtain an organic extract, and then said azeotropic solvent is distilled off to obtain hydroxyalkyl monoacrylate.

16. A process according to claim 1, wherein said hydroxyalkyl monoacrylate is produced by subjecting said acrylic acid derivative represented by the general formula (I) and said alkane diol represented by the general formula (III) to transesterification.

17. A process according to claim 16, wherein said acrylic acid derivative represented by the general formula (I) is methyl acrylate.

18. A process according to claim 1, wherein said esterification, transesterification or combination of esterification and transesterification is conducted at a temperature of 70 to 130° C.

* * * * *